United States Patent [19]
Simpson

[11] 4,452,358
[45] Jun. 5, 1984

[54] MEDICAL APPLIANCE DISPOSAL CONTAINER

[76] Inventor: James L. Simpson, 307 MacLaren La., Lake Bluff, Ill. 60044

[21] Appl. No.: 522,618

[22] Filed: Aug. 12, 1983

Related U.S. Application Data

[63] Continuation-in-part of Ser. No. 354,951, Mar. 5, 1982, Pat. No. 4,410,086.

[51] Int. Cl.³ .................. B65D 25/00; B26F 3/00; B65F 7/00; B65F 1/02
[52] U.S. Cl. .................. 206/366; 206/63.5; 206/380; 206/216; 206/459; 225/93; 241/99
[58] Field of Search .................. 206/366, 63.5, 380, 206/370, 365, 216, 459; 225/93; 241/99

[56] References Cited

U.S. PATENT DOCUMENTS

| | | | |
|---|---|---|---|
| 819,678 | 5/1906 | Simmons | 206/63.5 |
| 2,034,006 | 3/1936 | Smith | 206/63.5 |
| 3,226,007 | 12/1965 | Thies et al. | 206/365 |
| 3,469,750 | 9/1969 | Vanderbeck | 241/99 |
| 3,683,733 | 8/1972 | Johan et al. | 241/99 |
| 3,796,359 | 3/1974 | Dick | 206/365 |
| 3,851,555 | 12/1974 | Eldridge et al. | 241/99 |
| 3,893,608 | 7/1975 | Koenig | 206/366 |
| 3,938,745 | 2/1976 | Gladwin | 241/99 |

*Primary Examiner*—William T. Dixson, Jr.
*Attorney, Agent, or Firm*—Thomas W. Speckman

[57] ABSTRACT

A medical appliance disposal container is disclosed having at least one opening for insertion of medical appliances, the opening being covered by at least one slotted plastic membrane for insertion of the desired medical appliance into the disposal container. In at least one of the openings at the end of the slot is a needle destruction means whereby needles may be destroyed while attached to a syringe and the destroyed needle-syringe assembly inserted through the slot into the disposal container. In another embodiment, laminated plastic screens can be color-coded to aid in sorting and counting of medical appliances, such as scalpel blades, following surgery. The disposal container of this invention provides for the direct intact disposal of a wide variety of medical appliances while providing an inexpensive container for placement at a large number of locations throughout a health care facility. The medical appliance disposal container disclosed reduces the risk of contents spillage should the container be upset during use.

21 Claims, 13 Drawing Figures

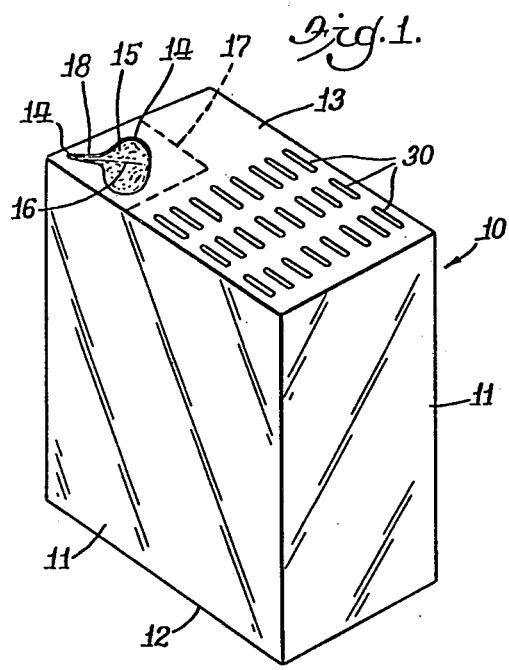
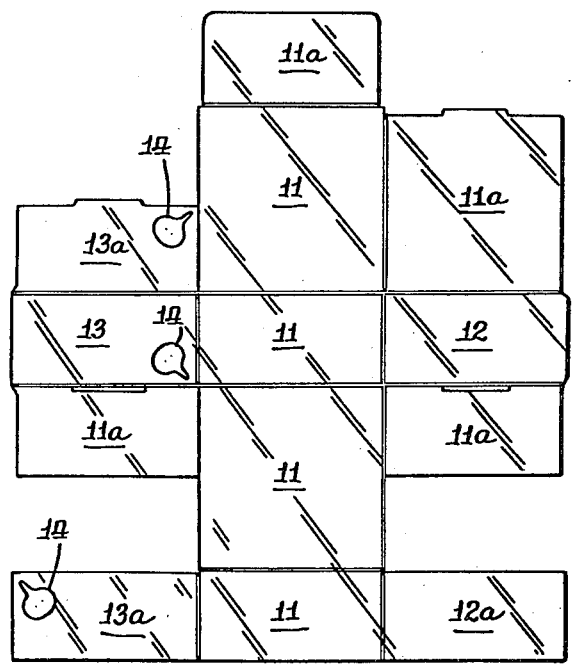
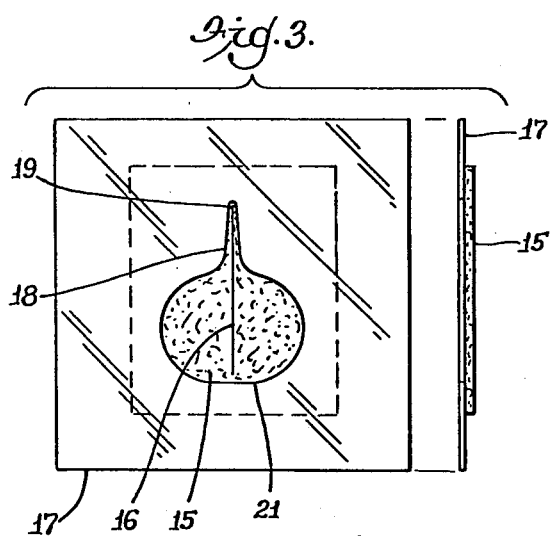
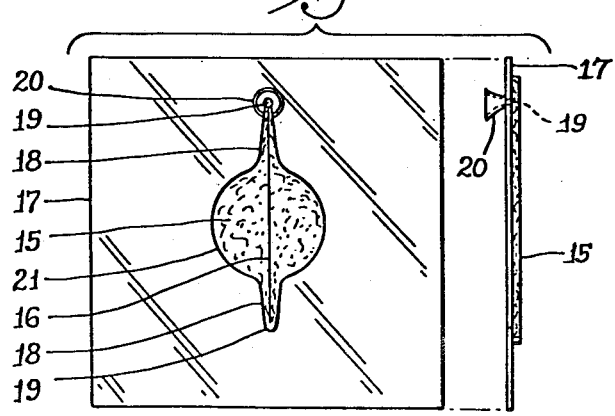
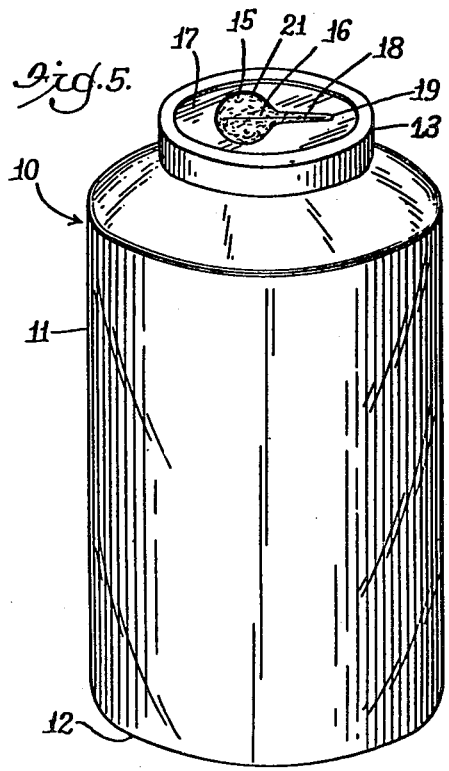

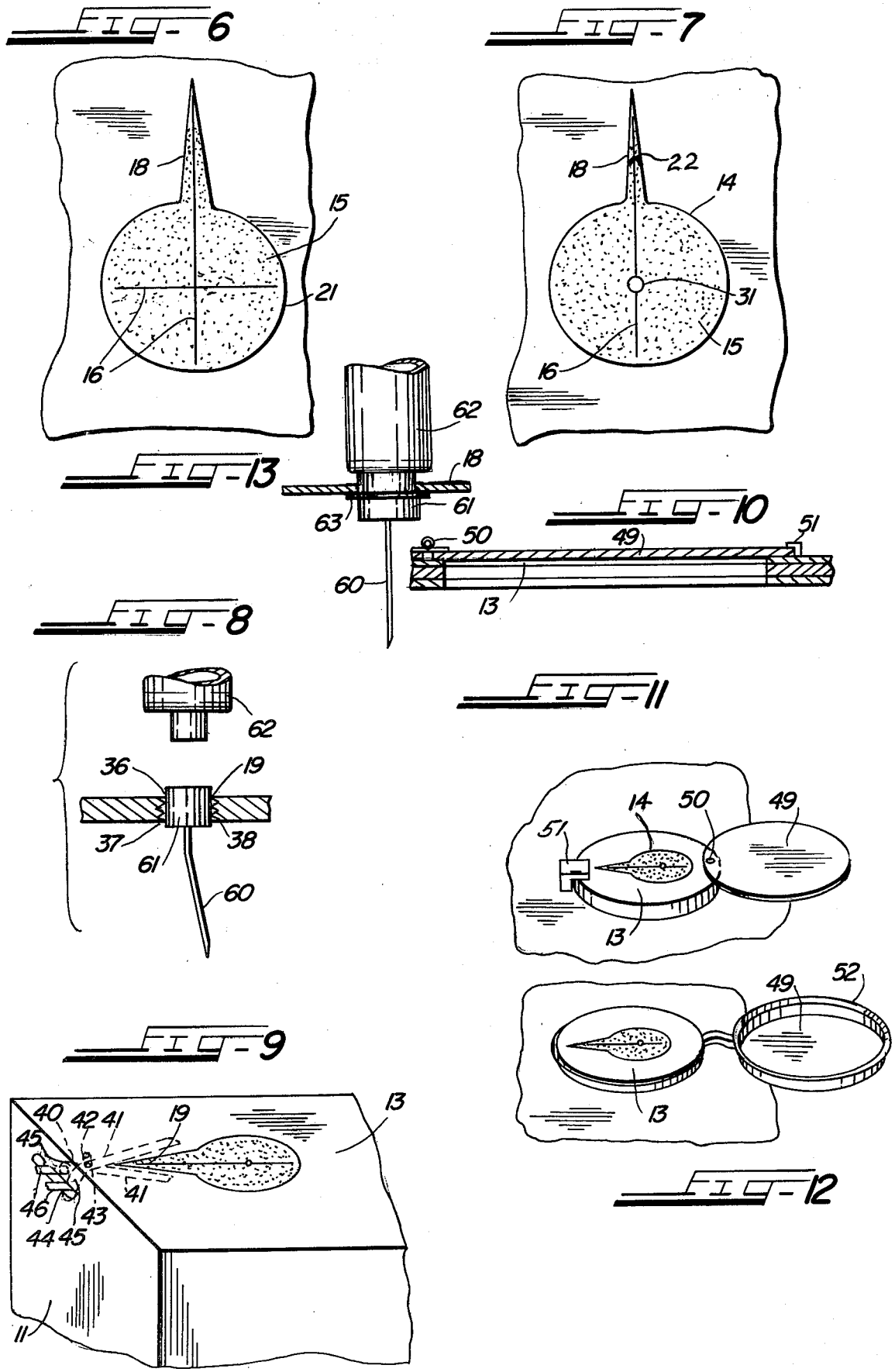

MEDICAL APPLIANCE DISPOSAL CONTAINER

This application is a continuation-in-part of my co-pending application, Ser. No. 354,951 filed Mar. 5, 1982 now U.S. Pat. No. 4,410,086.

BACKGROUND OF THE INVENTION

1. Field of the Invention

This invention relates to medical, dental and veterinary appliance disposal, hereinafter referred to as medical to include all fields. More particularly this invention relates to an improved apparatus for the safe disposal of potentially injurious medical appliances such as needles, syringes, scalpel blades, laboratory culture slides, blood tubing and toxic waste containers.

2. Description of the Prior Art

Potentially contagious medical waste, such as scalpel blades and particularly syringes with needles present an imminent threat of injury to patient-care personnel. Accidental needle puncture is the most frequent accident in hospitals. The Bacterial Diseases Division, Bureau of Epidemiology, Center for Disease Control, advises that disposal apparatus for such waste should be rigid containers; placed in each patient room; syringes with needles should be placed directly into the disposal container without disassembling needle from syringe; and full containers should be securely taped shut to provide safe storage prior to final disposal with other solid waste from the hospital. Contagious medical waste of the above nature presents an even more serious problem of disposal and specialized handling. Prior disposal containers, particularly for scalpel blades and syringes and needles, have been largely unable to meet the above criteria.

Prior disposal methods for medical waste have been of several types. One type requires the user to insert the needle into an external clipping device which shears the needle. However, the syringe must be placed separately into a disposal container. Since the external clipping device requires two hands to operate, the user must have both hands free to dispose of a needle and syringe. Moreover, the external clipping device may dull and then is likely to splatter the immediate area with blood or other syringe contents. The clipping or snapping disposal techniques air mobilize microorganisms or other contaminants. Other similar methods involve chopping the assembled needle and syringe into pieces or recapping the needle and manually breaking the assembly prior to disposal. These methods result in added exposure to health care personnel.

A second general means of disposal has used a corrugated cardboard container with a slot in the top panel through which the user inserts the appliance for disposal. This type of disposal container does not include a clipping or other means for making the syringe needle inoperable. Furthermore, since the receiving slot remains open while the container is in use, there is a chance the contents could be spilled if the disposal container was upset.

SUMMARY OF THE INVENTION

This invention provides an improved apparatus for the safe disposal of potentially injurious medical appliances such as needles, syringes and scalpel blades. The medical appliance disposal container of this invention includes a bender or internal clipping means mounted in the top panel region of the disposal container, for bending or clipping needles. In one embodiment, a bender plate has a central opening sufficiently large to receive the entire medical appliance, and a tapered slot leading to a needle bending orifice. After bending the needle, the user can directly deposit the needle-syringe assembly without withdrawing the needle from the disposal container or separating the needle from the syringe. A single or multi-slotted film laminated, reticulated polyurethane foam screen and a plastic membrane cover having a central needle orifice spans the bender plate opening, guides the needle to the bending orifice, and prevents spillage should the disposal container be upset during use. To provide an added measure of safety, an external closure means, such as a hinged or snap top cover, may be provided to securely close the opening of the container to further seal against discharge of toxic, pathenogenic or carcinogenic matter to the atmosphere. The laminated screens can be colorcoded to aid in the sorting and counting of medical appliances, such as scalpel blades, following surgery.

In another embodiment of this invention, where reusable syringes are used, the throat opening of the needle bending orifice of this invention is tapered and contains a saw-tooth inner diameter geometry so that after insertion into the orifice and bending, as the syringe-needle assembly is withdrawn, the saw-teeth grasp the needle barrel allowing syringe withdrawal only. The needle barrel and needle are retained and deposited inside the container.

In another embodiment of this invention, where reusable syringes are used, a flexible slotted membrane, with a scalloped, waffled, teethed or serrated inner lining spans the guide means and provides an adhesion means to grasp and hold the needle barrel hub so that when the needle hub is pressed into the guide area and twisted, the needle barrel and hub separate and fall into the container.

In another embodiment, an interal clipping means is provided to allow the user to shear off the needle while the needle is inside the disposal container. A slotted guide plate, of the sort disclosed above, positions the needle between the shear blades. The user actuates the internal clipper by external means to shear the received needle. Thus, all contaminants resulting from the needle destruction are confined inside the disposal container. After needle shearing, the remaining syringe elements may be disposed of into the container in the usual fashion of this invention.

In another embodiment of this invention materials of sufficient strength and density and impermeable to needle punctures, such as fiber board, may be utilized as an integral structure to provide the needle bending means, thus eliminating the requirement for a separate bender plate as disclosed above. The top panel of the container is fabricated to provide a rigid guide and bending orifice member to receive and allow bending of the needle and also syringe disposal in substantially the same manner as that disclosed where a bending plate is used. By eliminating the bending plate, the number of fabrication and assembly steps required to manufacture the container of this invention is significantly reduced.

The inexpensive medical appliance disposal container of this invention is not limited to contagious waste and can be easily autoclaved prior to final disposal.

It is an object of this invention to provide an improved container for the safe disposal of potentially injurious medical appliances which overcomes many of the disadvantages of prior apparatus.

It is another object of this invention to provide a means for safe disposal of medical appliances which protects staff or paramedical persons from accidental needle puncture.

It is another object of this invention to provide a disposal container for the direct intact disposal of a wide variety of medical appliances.

It is still another object of this invention to provide a single disposal container capable of rendering needles inoperable.

It is yet another object of this invention to provide an inexpensive medical appliance disposal container for placement in each patient room.

It is still a further object of this invention to provide a medical appliance disposal container that reduces the risk of contents spillage should the container be upset during use.

It is another object of this invention to provide a medical appliance disposal container which shows the number of such appliances which have been inserted therein.

These and other objects, advantages and features of this invention will become apparent from the description together with the drawings.

BRIEF DESCRIPTION OF THE DRAWINGS

FIG. 1 is a perspective view of a medical appliance disposal container of one embodiment of this invention;

FIG. 2 is a flat plan view of a collapsible disposal container of one embodiment of this invention;

FIG. 3 is a top and side view showing one embodiment of a bender plate according to this invention;

FIG. 4 is a top and side view of another embodiment of a bender plate of this invention;

FIG. 5 is a perspective view of a medical appliance disposal container of another embodiment of this invention;

FIG. 6 is a top view showing another embodiment of a bender means according to this invention;

FIG. 7 is a top view of another embodiment of a bender means according to this invention;

FIG. 8 is a side view showing a syringe needle inserted in a needle bending orifice of one embodiment of this invention;

FIG. 9 is a perspective view of a medical appliance disposal container showing an internal clipping means of one embodiment of this invention;

FIG. 10 is a side view showing a top closure means of one embodiment of this invention;

FIG. 11 is a perspective view showing another closure means according to this invention;

FIG. 12 is a perspective view showing yet another closure means according to this invention; and FIG. 13 is a side view of a reusable syringe-needle assembly showing the needle barrel hub positioned below the guide plate in accordance with one embodiment of this invention.

DESCRIPTION OF THE PREFERRED EMBODIMENTS

FIG. 1 shows medical appliance disposal container 10 with an enclosed body portion of side walls 11, bottom 12, and top 13. It is apparent that the container top may be of separate construction or may be part of the body construction. Top 13 has container opening 14 of sufficient size for insertion of a needle-syringe assembly therethrough into the inside of the container. In association with and of the same general size as container opening 14, is syringe disposal opening 21 in bending means plate 17. As best seen in FIGS. 3 and 6, syringe disposal opening 21 is covered or spanned by at least one plastic membrane 15. Plastic membrane 15 has one or more slots 16 of sufficient size to permit insertion of the desired medical appliance into disposal container 10. One of slots 16 extend substantially to the end of bending means guide slot 18 in bending means plate 17. At the end of bending means guide slot 18 a bending means orifice 19 may be placed wherein a needle mounted on a syringe may be readily bent, prohibiting further use.

In FIG. 7, a needle orifice is shown, 31, central to the container opening 14. In this embodiment of this invention an orifice opening 31 is provided for needle insertion so as to avoid the accidental puncturing and contamination of the plastic membrane 15.

It is thus seen from FIGS. 1, 3 and 7 that the needle of an intact needle-syringe assembly may be inserted through slot 16 and/or needle orifice 31, moved along guide slot 18 to bending orifice 19, easily bent, moved back out of guide slot 18 and the entire needle and syringe, while still assembled, deposited into the disposal container through slot 16. In a similar fashion, a bending plate may have the configuration as shown in FIG. 4 wherein the bending means orifice 19 has a bending orifice ferrule 20 extending therefrom to provide yet easier bending of the needle and to make possible the use of thinner and less stiff material for bending plate 17.

In another embodiment of this invention, medical appliance disposal container 10 may be a molded plastic container such as shown in FIG. 5 having side walls 11, bottom 12 and separate top 13. In the embodiment as shown in FIG. 5, it is readily seen that top 13 is covered by bending means plate 17 with syringe disposal opening 21, bending means guide slot 18, and bending means orifice 19, all covered by membrane 15 having slot 16 extending the length of the guide slot to the bending orifice 19. Again, any medical appliance which will fit through slot 16 may be placed in disposal container 10 and needles of needle-syringe assemblies may be inserted into slot 16 to about half their length, moved along guide slot 18 to bending orifice 20 where the needle is readily bent, and the assembly moved back along slot 16 with the needle being below membrane 15 to the central portion of syringe disposal opening 21 where the syringe body may be inserted into disposal container 10.

FIG. 2 shows the layout of a collapsible container according to one embodiment of this invention which provides a full liner for the container. The collapsible container shown collapsed in FIG. 2 has the assembled shape of the container shown in FIG. 1 with the side walls 11, bottom 12 and top 13, side wall liners 11a, bottom liner 12a and two top liners 13a. In a collapsible container of this type which may be readily and cheaply constructed of cardboard, bending means plate may be aligned with container opening 14 and sandwiched between top panel 13 and liner panel 13a, or between the liner panels, preferably with adhesive means to retain the bender plate in alignment with top hole 14.

In another embodiment of this invention, a collapsible container, such as that shown in FIG. 2, is fabricated of materials of sufficient yield strength to withstand needle bending forces applied directly against the top container wall. The medical appliance container of this invention is fabricated out of material, such as fiberboard, dense enough to prevent needle punctures and of sufficient enough strength to provide a rigid bending means to withstand the bending force of the needle as it is inserted and bent against bending means guide slot 18 in the container wall itself. The bending means of this embodiment is designed integrally into the top container wall during container fabrication wherein the bending means guide slot 18 is cut in the top container wall which itself serves as the bending means. The geometrical configuration of the bending means may vary generally as previously disclosed in regard to bender plates 17, and which have been generally depicted in FIGS. 3 and 4.

In a fashion substantially similar to where a bending means plate is utilized, a tapered guide slot 18, bending orifice 19 and slotted cover membrane 15 may be provided in combination with a fiberboard container construction to accomplish the bending and disposal of the needle-syringe assembly and to accomplish other disclosed objects of this invention.

Medical appliance disposal container 10 shown in FIG. 1, in addition to the syringe needle bending opening and syringe disposal opening previously described also has medical appliance insertion openings 30. The medical appliance insertion openings 30 may be of any suitable shape to receive particular medical appliances. The medical appliance insertion openings 30, like syringe disposal opening 21, have a slotted plastic membrane covering the opening with the slot being of sufficient size to permit insertion of the desired medical appliance into the disposal container. For different medical appliances, it is convenient to have rows of openings 30 for each type of medical appliance. Further, it is particularly desirable to have the plastic membranes covering the medical appliance insertion openings 30 color-coded so that the membrane at each opening will indicate disposal of a medical appliance through that opening providing accurate count of appliances used and disposed of as will be further discussed below.

From the above general description of the medical appliance disposal container of this invention, it is apparent that a wide variety of shapes and sizes of containers may be used to fit a wide variety of specific use situations. For example, a disposal container as shown in FIGS. 1 and 2 may be fabricated from inexpensive cardboard or fiberboard in appropriate sizes to accommodate use in private hospital rooms, large wards, nursing stations, and specific treatment or operating rooms, as well as emergency vehicles, ambulances, and the like. The cardboard or fiberboard container may be coated on its interior with an absorbent material to absorb liquids or it may be coated on its interior with an absorbent resistant material to prevent leakage of liquids. Likewise, the exterior may be coated with a plastic to prevent liquid absorption and to provide easy and effective cleaning. It is readily seen that synthetic polymeric sheet material of sufficient stiffness may be substituted for cardboard in the disposal box shown in FIG. 1. Currently available blow molded plastic containers such as bottles having the shape generally shown in FIG. 5, may also be used in instances where the disposal container needs to be liquid-proof. Use of the plastic bottle-type disposal container as shown generally in FIG. 5, permits utilization of a wide number of different disposal openings by simply providing different inserts for seating beneath cap 13.

Bending means plate 17 may be used in connection with container openings 14 through which it is desired to dispose of needle-syringe assemblies. As described above, the bending plate provides bending orifice 19 for bending the needle while attached to the syringe and syringe disposal opening 21 of sufficient size to permit passage of the syringe body therethrough. There are many shapes and sizes of bending plates which would be suitable for use with the disposal containers of this invention as is readily apparent to one skilled in the art upon reading this disclosure. Generally, for durability, it is desirable that the bending plate be of a metallic material, but wood chip fiberboard and synthetic polymeric materials may also be used, particularly glass fiber reinforced sheet materials, such as glass reinforced nylon or durable plastics such as Lexan, a polycarbonate. For thinner bending plates and for bending plates constructed of materials which are less durable, it is preferable to provide bending orifice ferrule 20, as shown in FIG. 4, of metal to provide a durable bending orifice permitting direct one-handed bending and disposal of a needle-syringe assembly. Also, as shown in FIG. 4, the bending means may have multiple bending orifices each with their appropriate guide slot for reception of different size or different types of needles.

Syringe disposal opening 21 is completely covered by at least one slotted plastic membrane. Plastic membrane 15 preferably has a single slot 16 which extends substantially across bending means opening 21, along bending means guide slot 18 and bending orifice 19. To allow disposal of medical appliances of significant girth, plastic membrane 15 may contain multiple slots 16 as shown in FIG. 6. Plastic membrane 15 is preferably sheet reticulated synthetic polymeric foam of a type which returns to its original condition following spreading of slot 16 upon insertion of a medical appliance. Suitable such films include reticulated polyurethane foam and polyvinylchloride. Multiple layers of spaced plastic membranes may be used, such as one on each side of a bending means plate or attached to container opening 14 and different top liners 13a as shown most clearly in FIG. 2. Multiple membranes, such as two or three, assure closure of the membrane following insertion of the medical appliance therethrough and provide additional strength to the open enclosure when the disposal container may be accidentally turned upside down. The single slot 16 also aids in retention of medical appliances within the disposal container when it is turned upside down. The surface of plastic membrane 15 facing the exterior of the disposal container may be a laminated smooth polymeric film for ease of cleaning.

Medical appliance insertion openings 30, used for medical appliances other than needle-syringe assemblies, may be constructed in the same fashion as described above except that the disposal opening need not provide the bending means guide slot 17 and bending means orifice 19. A bending means plate 17 is not necessary for such insertion openings. The plastic membrane may be constructed in a similar fashion and adhered directly to the bottom of container top 13 or preferably between top 13 and top liner 13a or between two layers of top liner 13a. Medical appliance insertion openings 30, of suitable shape for particular medical appliances, may be arranged in convenient rows for each type of medical appliance and slot 16 may be covered with a thin colored layer of sheet material which must be broken for insertion of the medical appliance and thus using a different hole for each medical appliance, the number of specific medical appliances inserted into the disposal container may be readily ascertained, as is necessary in various medical practices, such as insertion of scalpels from an operating procedure. It is also apparent that the opening or openings for disposal of medical appliances may also be located in the upper portion of the sides of the disposal container.

A suitable durable adhesive coated seal may be provided on the side or top of the disposal container for fully covering the openings in the top of the container for disposal of the complete container containing the disposed medical appliances. Any suitable means such as a hinged or snap top cover may be used to cover the container openings. As shown in FIGS. 10 and 11, the container cover top 49 may be hinged by pivot 50 at any suitable location about the perimeter of the opening. When the container is ready for disposal, the container cover top 49 may be positioned over container top 13 or only over container top opening 14 and secured with safety closure latch means 51. As shown in FIGS. 11 and 12, top cover 49 may be any suitable flexible material, such as plastic, with lip region 52 of such outer diameter dimension to engage closure latch means 51 shown in FIG. 11 or, as shown in FIG. 12, to snugly fit over the outer diameter of the top 13, to provide an airtight secured cover. The medical appliance disposal container can then be safely disposed of in accordance with recommended procedures, depending upon its contents. Contagious medical waste may be disposed of in containers according to this invention which can be autoclaved as required prior to final disposal.

In another embodiment of this invention, a means is provided to allow the user to bend and dispose of the needle and withdraw the syringe without the requirement of the removal of the needle from the confines of the container. In FIG. 8, bending orifice 19 is shown having a gradually tapering inner diameter which is wider at its top region 36 and which gradually narrows to its bottom region 37. The inner diameter of the orifice is uniformly teethed 38. The teeth are unidirectionally flexible when a downward force is applied and are structurally resistant when an upward force is applied through the orifice 19. In operation, when needle 60 and needle barrel 61 assembly are inserted through the top region 36 of the orifice 19, and forced downward upon the teethed 38 region, the teeth flex to increase the relative inner diameter of the orifice opening allowing continued downward travel of the needle barrel 61. Downward travel of the needle barrel 61 stops once the syringe body 62 contacts the top region 36 of the orifice opening.

When the syringe body 62 is withdrawn upward, the teeth return to their unflexed state thereby narrowing the inner diameter of the orifice opening. As more force is applied to withdraw needle barrel 61 the teeth bite into the needle barrel 61 causing a restraint force to the needle barrel 61 removal. Eventually the upward or withdrawal force of the syringe body 62 exceeds the friction force holding the needle barrel 61 to the syringe body 62 and the needle barrel 61 remains within the confines of the grasp of the orifice teeth 38 as the syringe body 62 is withdrawn. The features of this embodiment allow the user to insert the needle into the bending orifice 19, bend the needle 60, then insert the needle barrel into the orifice and withdraw only the reusable syringe body 62 without exposing the user to needle contamination.

In another embodiment of this invention, as shown in FIGS. 7 and 13, where reusable syringe cartridges are used, a means is provided to allow separation of the syringe needle 60, barrel 61 and hub 63 from syringe body 62 while needle 60 is inside the container. In operation, the plastic membrane 15, as best shown in FIG. 7, is provided an orifice 31, of sufficient size to allow needle 60, needle barrel 61 and needle barrel hub 63 to pass through into the container. After the needle barrel hub 63 is inserted into the container, the entire syringe-needle assembly is moved into guide slot 18 to its furthest point within the guide slot 18. At this point, the syringe body 62 is lifted upward by the user until top region of needle barrel hub 63 contacts the lower region of guide 18. With an upward force applied to the syringe body 62 the user turns the syringe body 62 in a fashion about its central axis. The resulting adhesion friction force between the top syringe hub 63 and lower guide 18 causes the needle hub 63, barrel 61 and needle 60 to release and fall into the container. Once removed, the syringe body 62 may be removed for reuse.

In another embodiment of this invention, as shown in FIG. 7, the top cover membrane is cupped at any suitable region 22 to span the throat of the guide means 18. The membrane surface is either teethed, scalloped, waffled or serrated to provide an adhesion surface when in communication with the needle barrel hub 63.

In operation, the syringe-needle assembly is inserted through orifice opening 31 to a point wherein the membrane spans the needle hub 63. The syringe-needle assembly is guided along the slot 16 into the guide 18, to its furthest point against the cupped region of the membrane span 22. The teethed, scalloped, waffled, or serrated surface of the membrane span 22 wraps about the needle hub 63.

The adhesion friction force between the membrane span surface 22 and the needle hub 63 allows the user to turn the syringe body 62 while the needle 60, needle barrel 61 and needle barrel hub 63 remain stationary within the membrane span 22. Eventually, the syringe body is released allowing the needle hub 63, needle barrel 61 and needle 60 to fall inside the container. The syringe body 62 is easily withdrawn for subsequent use.

In another embodiment of this invention, as shown in FIG. 9, an internal clipping means is provided so that a needle, while inserted inside the container, can be sheared. The clipper 40 may be of any suitable design having shearing blades 41. The clipper 40 is suitably located within the container and preferably directly beneath bending orifice 19 inside the container, to receive the needle directly between the shearing blades 41 when inserted through the orifice 19. The blade shears are aligned relative to the orifice opening 19 by means such as an adjustable rod member 42 fastened to the pivot point 43 of the clipper and to the top container wall 13 guide. To provide horizontal stability and a means to actuate the opening and closing of the clipper blades 41, a guide means 44 in the side wall 11 container member is provided. The lever arm extensions 45 of each blade are positioned within the guide and are free to travel within the confines of the guide 44 to open and close the clipper blades 41. A flexible plastic sheet or rubber grommet or other sealing means is attached to the side wall 11 to seal off the guide means 44 to prevent escape of the contents of the container. In operation, after the user places the needle 60 into the orifice 19, wood dowels 46 or other extensions are placed into the actuator means and simultaneously moved inward causing blade closure and shearing of the needle.

One feature of this embodiment allows the user to destroy and dispose of used needles, while needle contaminants are contained with the disposal vessel. Also, the complete shearing of used needles in this fashion prevents needle re-use by one scavenging the contents of the container.

An improved medical appliance disposal container has been described which protects health service personnel from needle puncture wounds, the most prevalent hospital accident. Further, the disposal container of this invention provides direct intact disposal of a wide variety of medical appliances; renders needles inoperable; reduces risk of contents spillage; and provides an inexpensive disposal container for wide usage in the health care industry.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

I claim:

1. A medical appliance disposal container comprising; a container body comprising a bottom and side walls; and a container top enclosing said container, said container top having at least one opening therein for insertion of medical appliances, said opening being covered by at least one slotted plastic membrane, said slot being of sufficient size to permit insertion of the desired medical appliance into the disposal container, and a needle destruction means located at one end of said slot whereby needles may be rendered unusable while attached to a syringe and the destroyed needle-syringe assembly inserted through said slot into said disposal container.

2. The medical appliance disposal container of claim 1 wherein said destruction means comprises a tapered orifice with a teethed inner diameter.

3. The medical appliance disposal container of claim 1 wherein said container body, top, walls and needle destruction means comprises one piece of material which is capable of being assembled to form said container from a flat sheet.

4. The medical appliance disposal container of claim 3 wherein said container body, top, bottom, walls, and destruction means guide, are fabricated from fiberboard.

5. The medical appliance disposal container of claim 1 wherein said plastic membrane having single or multiple slots is provided a central orifice of sufficient size to permit needle, needle barrel and needle hub insertion.

6. The medical appliance disposal container of claim 1 wherein said container top opening is covered by a hinged top cover.

7. The medical appliance disposal container of claim 1 wherein said container top opening is covered by a snap top cover.

8. The medical appliance disposal container of claim 1 wherein said needle destruction means comprises an internal clipping means consisting of internal shear blades and an external actuating means and alignment means to align the medical appliance between said shear blades prior to destruction.

9. The medical appliance disposal container of claim 1 wherein the surface of said membrane is formed to provide a gripping means.

10. The medical appliance disposal container of claim 9 wherein said membrane spans the throat opening of the guide means.

11. The medical appliance dispoal container of claim 1 wherein said needle destruction means comprises a bending means.

12. The medical appliance disposal container of claim 11 wherein said bending means is an integral part of said top of said container.

13. The medical appliance disposal container of claim 12 wherein said bending means comprises an orifice and an orifice ferrule extending outwardly therefrom.

14. The medical appliance disposal container of claim 1 having additional openings in said top for insertion of medical appliances, said additional openings being covered by at least one slotted plastic membrane, said slot being of sufficient size to permit insertion of the desired medical appliance into the disposal container.

15. The medical appliance disposal container of claim 14 wherein said additional openings are color-coded so that the membrane at each opening will indicate disposal of a medical appliance through that opening.

16. The medical appliance disposal container of claim 15 having said slot covered by a thin colored layer of sheet material which is broken upon insertion of a medical appliance.

17. The medical appliance disposal container of claim 1 wherein said plastic membrane is selected from the group consisting of reticulated polyurethane foam and polyvinylchloride.

18. In a medical appliance disposal container of the type having at least one opening therein for insertion of a medical appliance, the improvement comprising; said opening being covered by at least one slotted plastic membrane, said slot being of sufficient size to permit insertion of the desired medical appliance into the disposal container, and a destruction means located at one end of said slot whereby needles may be bent while attached to a syringe and the bent needle-syringe assembly inserted through said slot into said disposal container.

19. In a medical appliance disposal container of claim 18 wherein said destruction means is a bending means which is an integral part of said top of said container.

20. In a medical appliance disposal container of claim 18 wherein said destruction means comprises a tapered orifice with a teethed inner diameter.

21. In a medical appliance disposal container of claim 18 wherein said needle destruction means comprises an internal clipping means consisting of internal shear blades and an external actuating means and alignment means to align the medical appliance between said shear blades prior to destruction.

* * * * *